(12) United States Patent
Van Doorn et al.

(10) Patent No.: US 6,492,549 B2
(45) Date of Patent: Dec. 10, 2002

(54) PROCESS FOR PREPARING ALKYLENE DIAMINE TRIACETIC ACID

(75) Inventors: Marcellinus Alexander Van Doorn, Goor (NL); Johannes Wilhelmus Driessen, Nederweert (NL); Tjerk Oedse Boonstra, Duiven (NL); Martin Heus, Arnhem (NL)

(73) Assignee: Akzo Novel NV (NL)

( * ) Notice: Subject to any disclaimer, the term of this patent is extended or adjusted under 35 U.S.C. 154(b) by 0 days.

(21) Appl. No.: 09/753,150

(22) Filed: Jan. 2, 2001

(65) Prior Publication Data

US 2001/0007042 A1 Jul. 5, 2001

Related U.S. Application Data

(60) Provisional application No. 60/181,264, filed on Feb. 9, 2000.

(30) Foreign Application Priority Data

Jan. 5, 2000 (EP) .............................................. 00200023

(51) Int. Cl.$^7$ ............................................ C07C 229/00
(52) U.S. Cl. ....................................... 562/565; 562/566
(58) Field of Search ................................. 562/565, 566

(56) References Cited

U.S. PATENT DOCUMENTS 5,250,728 A * 10/1993 Parker et al. ................ 562/565

FOREIGN PATENT DOCUMENTS

EP 0 546 867 6/1993 ......... C07C/229/16

OTHER PUBLICATIONS

Gary L. Blackmer, et al., "Synthesis of Ethylenediamine—N,N,N'–triacetic Acid and Its Cobalt (III) Complexes", Journal of the American Chemical Society vol. 91, No. 9, Apr. 23, 1969, pp. 2400–2401.

* cited by examiner

Primary Examiner—Mukund J. Shah
Assistant Examiner—Zacharey C. Tucker
(74) Attorney, Agent, or Firm—Richard P. Fennelly

(57) ABSTRACT

A process for the preparation of alkylene diamine triacetic acid (derivatives) which comprises the conversion of an alkylene diamine (derivative) to a metal salt of an alkylene diamine triacetic acid (derivative). The reaction is carried out in the presence of a polyvalent metal ion $M^{a+}$ and the entire reaction is carried out under hydrolyzing conditions if any of the reactants contain or form nitrile or amide groups.

11 Claims, No Drawings

PROCESS FOR PREPARING ALKYLENE DIAMINE TRIACETIC ACID

This application claims the benefit of European Patent Application No. 00200023.0, filed Jan. 5, 2000, and U.S. Provisional Application No. 60/181,264, filed Feb. 9, 2000.

BACKGROUND OF THE INVENTION

The present invention relates to a process for preparing alkylene diamine triacetic acid (derivatives).

Alkylene diamine triacetic acid (derivatives), such as ethylene diamine triacetic acid and its salts, have applications in the field of chelating chemistry, such as metal cleaning. A process for preparing ethylene diamine triacetic acid is known from EP 0,546,867. The process disclosed in this reference starts from pure ethylene diamine-N,N'-diacetic acid and comprises four reaction steps, viz.

(i) contacting ethylene diamine diacetic acid or salts thereof, preferably the sodium salt, with formaldehyde
(ii) reacting the resulting product with a cyanide source to form a mononitrile diacid,
(iii) hydrolyzing the product of step (ii) and where necessary cyclizing the resulting monoamide diacetic acid to a ketopiperazine diacid, and
(iv) reacting the resulting ketopiperazine diacetic acid with an alkali metal or alkaline earth metal hydroxide, preferably sodium hydroxide, to obtain ethylene diamine triacetic acid.

The process of this reference thus comprises four individual process steps. It is an object of the present invention to reduce the number of process steps.

Further, the starting material of this process, viz. ethylene diamine diacetic acid, is difficult to synthesize and thus expensive. More in particular, the synthesis of ethylene diamine diacetic acid requires a two-step process: ethylene diamine diacetic acid is either synthesized by the reaction of ethylene diamine with formaldehyde and cyanide with subsequent saponification of the resulting nitrile or by the reaction of ethylene diamine with glyconitrile (HO—CH—CN) with subsequent saponification of the resulting nitrile. It is noted that if any one of these reactions is carried out in a single process step, mixtures of ethylene diamine monoacetic acid, ethylene diamine diacetic acid, and ethylene diamine triacetic acid are obtained. Consequently, to obtain pure ethylene diamine diacetic acid such as is needed as starting material in the above process, a two-step process is indispensable. This makes the synthesis of the starting material quite sophisticated. It is therefore a further object of the present invention to employ a process where inexpensive and easily-synthesizable starting materials can be applied.

Finally, it is an object of the present invention to produce alkylene diamine triacetic acid in high purity.

SUMMARY OF THE INVENTION

It has now surprisingly been found that all the above objectives can be met by a process which comprises the conversion of an alkylene diamine (derivative) to a salt of an alkylene diamine triacetic acid (derivative), wherein the reaction is carried out in the presence of a polyvalent metal ion $M^{a+}$ and the entire reaction is carried out under hydrolyzing conditions if any of the reactants contain or form nitrile or amide groups.

DETAILED DESCRIPTION OF THE INVENTION

In particular, it has been found that if alkylene diamine (derivatives) are converted to alkylene diamine triacetic acid (derivatives) in the presence of polyvalent metal ions, the desired alkylene diamine triacetic acid (derivative) is obtained in high purity, whereas if monovalent metal ions instead of the polyvalent metal ions are applied in the same process, mixtures of alkylene diamine diacetic acid, alkylene diamine triacetic acid, and alkylene diamine tetraacetic acid (derivatives) result. In this case a further purification step is necessary to obtain alkylene diamine triacetic acid or a derivative thereof in high purity.

In the process of the present invention it is possible to form salts of the alkylene diamine triacetic acid (derivative) in a single process step starting from alkylene diamine. Consequently, the number of process steps can be reduced considerably and a starting material, viz. alkylene diamine, can be applied which is significantly less expensive than, e.g., the ethylene diamine diacetic acid used in the process of the above reference.

The invention will be described in more detail below. For convenience's sake, the following terminology will be used:
ADA: alkylene diamine
AD1A: alkylene diamine monoacetic acid
AD2A: alkylene diamine diacetic acid
AD3A: alkylene diamine triacetic acid
AD4A: alkylene diamine tetraacetic acid
EDA: ethylene diamine
ED1A: ethylene diamine monoacetic acid
ED2A: ethylene diamine diacetic acid
ED3A: ethylene diamine triacetic acid
ED4A: ethylene diamine tetraacetic acid The invention pertains to a process for preparing alkylene diamine triacetic acid (derivatives) which comprises the conversion of an alkylene diamine (derivative) of the formula

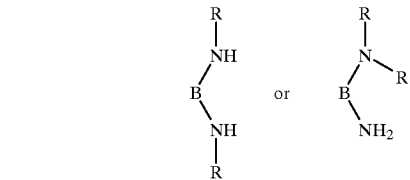

wherein B is selected from an unsubstituted or substituted alkylene bridge and R is independently selected from H or (salts of) —CH$_2$—COOH, —CH$_2$—CN, or —CH$_2$—CONH$_2$, to a salt of an alkylene diamine triacetic acid (derivative) of the formula

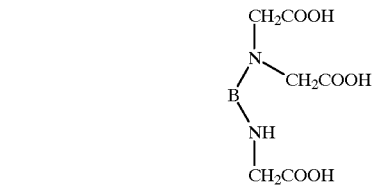

with the reaction being carried out in the presence of a polyvalent metal ion $M^{a+}$ and the entire reaction being carried out under hydrolyzing conditions if any of the reactants contain or form nitrile or amide groups.

Preferably, the alkylene bridge B in the ADA (derivative) starting material is an unsubstituted or substituted ethylene or propylene bridge. If the bridge is substituted, generally one or more of the bridging carbon atoms may be independently substituted by $C_1$–$C_6$ alkyl groups and preferably $C_1$–$C_4$ alkyl groups. It is preferred that the bridge is unsubstituted, and preferably B is selected from —CH$_2$—CH$_2$— or —CH$_2$—CH$_2$—CH$_2$— and more preferably B is —CH$_2$—CH$_2$—. In other words, a preferred ADA (derivative) is an EDA (derivative). Preferably, R stands for H and/or CH$_2$COOH moieties, with H being most preferred. The EDA (derivative) thus preferably comprises (salts of) ED2A, ED1A, and EDA, more preferably it comprises (salts of) ED1A and EDA, still more preferably it consists essentially of (salts of) ED1A and/or EDA, even more preferably it comprises (salts of) EDA, and most preferably it consists essentially of (a salt of) EDA.

The product of the process of the present invention is the salt of the AD3A (derivative). This salt consists at least in part of a complex of negatively charged AD3A (derivative) and the positively charged polyvalent metal ions. Of course, if further cations are present during the reaction, the salt may additionally comprise these cations apart from the complex. However, it is essential to the process of the invention that at least part of and preferably all of the AD3A (derivative) formed during the reaction is immediately complexed by the polyvalent metal ion. Without wishing to be bound by any theory, Applicant believes that due to the formation of this complex, the second still remaining NH function in the AD3A (derivative) is blocked. This NH function thus cannot be converted to an N—CH$_2$—COOH moiety and the formation of an AD4A (derivative) is therefore avoided. The process of the present invention thus makes it possible to prepare the AD3A (derivative) in high purity. It has been found that if, under the same reaction conditions, instead of the polyvalent metal ion, a monovalent metal ion such as sodium is used, AD4A is indeed formed apart from AD3A. Again without wishing to be bound by any theory, Applicant believes that monovalent metal ions are not able to form a complex wherein the remaining NH function is blocked. This is shown schematically below:

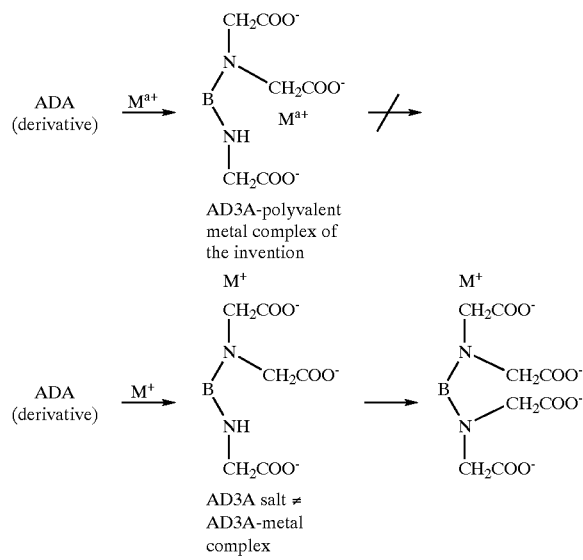

It is noted that, apart from the presence of the polyvalent metal ion, it is essential to the process of the invention that the entire reaction is carried out under hydrolyzing conditions if any of the reactants contain or form nitrile or amide groups. "Hydrolyzing conditions" in the sense of the present invention means that the reaction conditions are such that any nitrile and/or amide group added to the reaction mixture or formed during the reaction is instantaneously converted to a carboxylic acid moiety or the salt thereof. Generally, such hydrolyzing conditions are present when the pH is chosen to be above 9, preferably above 10, more preferably above 11, and most preferably above 12 during the entire reaction. Suitable pH values can be obtained by adding a base. Suitable bases are, e.g., the hydroxide of the polyvalent metal itself or an alkali metal hydroxide.

If nitrile or amide groups are present during the reaction, ammonia forms due to the hydrolysis of these groups. Therefore, at least when the reactants contain or form nitrile or amide groups, the reaction conditions are preferably chosen such that ammonia separates from the reaction mixture and can be removed. If atmospheric pressure is applied during the reaction, the temperature can be chosen, e.g., between 25° C. and the boiling temperature of the reaction mixture, preferably between 50° C. and the boiling temperature of the reaction mixture, more preferably between 70° C. and the boiling temperature of the reaction mixture, and most preferably it will be in the range of 100°–110° C. Alternatively, lower temperatures are possible if a lower pressure is applied.

The conversion from the ADA (derivative) to the AD3A (derivative) preferably is carried out in a single process step, meaning that no well-defined isolatable intermediate is formed during the reaction. Most preferably, the reaction is carried out in a one-pot process.

The process of the invention is not restricted to any particular reactants to be combined with the ADA (derivative) to form the salt of the AD3A (derivative).

In one process embodiment, the ADA (derivative) is reacted with a formaldehyde and a cyanide source in the presence of the polyvalent metal ion M$^{a+}$ under hydrolyzing conditions.

Suitable formaldehyde sources are, e.g., formaldehyde or paraformaldehyde. Suitable cyanide sources include gaseous hydrogen cyanide, an aqueous solution of hydrogen cyanide, and cyanide salts, e.g., alkali metal cyanide such as sodium cyanide or potassium cyanide and its aqueous solutions, or salts of the polyvalent metal ion and cyanide, such as calcium cyanide. Alternatively, it is possible to use a combined formaldehyde and cyanide source, i.e. a molecule which is converted to a formaldehyde and cyanide source under the reaction conditions. Such a combined formaldehyde and cyanide source is, e.g., glyconitrile.

As stated above, it is essential that in this process embodiment the reaction is carried out under hydrolyzing conditions. Preferably, the pH is chosen to be at least 9, more preferably at least 10, and most preferably at least 12 during the entire reaction process.

Without wishing to be bound by any theory, Applicant believes that non-hydrolyzing conditions lead to the formation of a reactive NH-containing AD3A derivative which contains nitrile or amide groups instead of free acid groups. It is further believed that such an AD3A derivative does not allow the formation of a complex with the polyvalent metal ion. The reactive NH function thus would not be blocked and the formation of an AD4A (derivative) would result. Contrary to the case where non-hydrolyzing conditions are applied, hydrolyzing conditions lead to the formation of the AD3A (derivative) of the present invention, which contains three carboxylic acid groups. As already set out above, this AD3A (derivative) is believed to form a complex with the polyvalent metal, thus blocking the reactive NH function and avoiding the formation of an AD4A (derivative). This is shown schematically below:

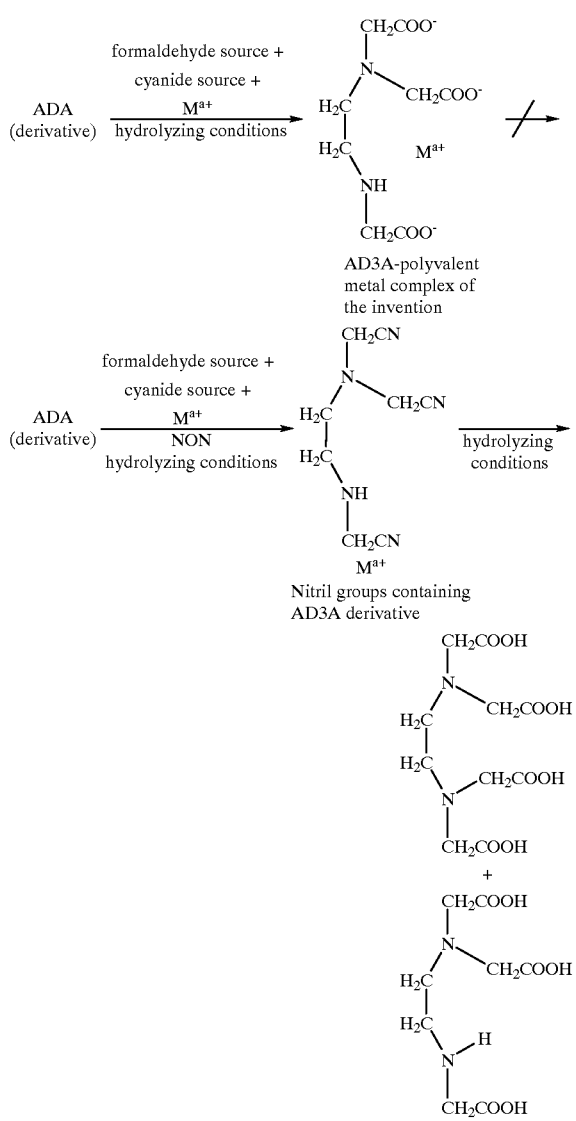

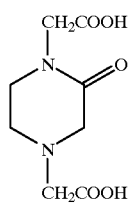

Incidentally, it is noted that in EP 0 546 867 the reactive NH function is blocked by choosing the reaction conditions such that in a first step a mononitrile diacid is formed and that subsequently the mononitrile compound is partially hydrolyzed to the amide, resulting in ketopiperazine diacetic acid which is isolated and finally hydrolyzed to ED3A. Consequently, during the first step the nitrile groups remain intact and thus no hydrolysis occurs; in the second step, the nitrile groups are partially hydrolyzed to amide groups which are entirely hydrolyzed in the third step. This is a very sophisticated process comprising several separate process steps with each process step being carried out at a very specific pH. Contrary thereto, in the process of the present invention, during the entire reaction the pH is chosen so high as will allow the instantaneous and complete hydrolysis of the nitrile and/or amide groups present during the reaction. The entire process control and in particular the pH control thus is much simpler than in EP 0,546,867. Further, the application of the process of the invention allows the reaction to be completed in a single process step. It is noted again that the fact that the entire reaction of the invention can be carried out under hydrolyzing conditions without the formation of an AD4A (derivative) is due to the presence of the polyvalent metal ion.

Due to the hydrolysis of the nitrile groups, ammonia is formed during the reaction. Therefore, as set out above, if atmospheric pressure is applied, the reaction temperature preferably ranges between 25° C. and the boiling temperature of the reaction mixture, more preferably between 50° C. and the boiling temperature of the reaction mixture, still more preferably between 70° C. and the boiling temperature of the reaction mixture, and most preferably it will be in the range of 100–110° C. Lower temperatures can be applied at lower reaction pressures.

The above process embodiment of the present invention is exemplified schematically below for EDA, ED1A, and ED2A as AD3A starting materials.

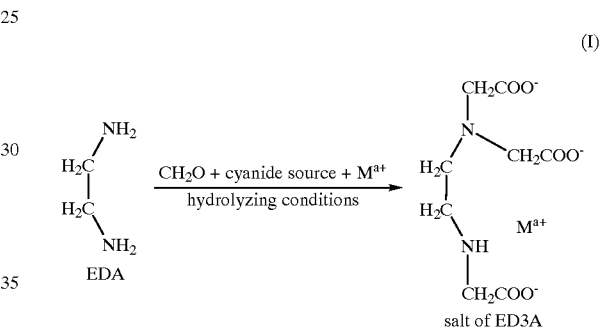

(I)

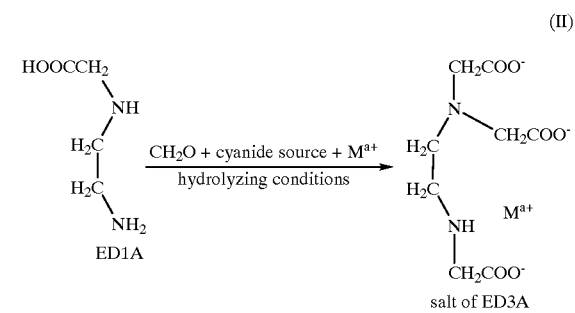

(II)

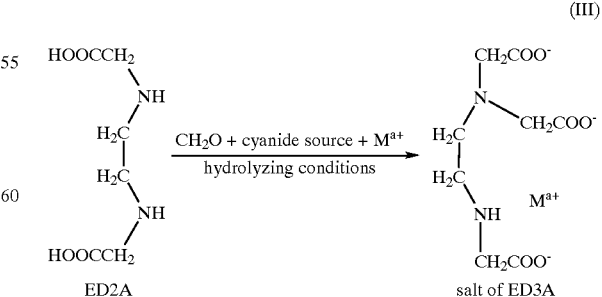

(III)

Preferably, the reactants are applied in a quantity ±10%, and more preferably ±5%, of the stoichiometric amount.

Most preferably, stoichiometric amounts of the reactants are applied. For the reactions illustrated above, this means that most preferably, 3 moles of formaldehyde and cyanide source each are applied per mole EDA (reaction I), 2 moles of formaldehyde and cyanide source each are applied per mole ED1A (reaction II), and one mole of formaldehyde and cyanide source each are applied per mole ED2A (reaction III).

Generally, all possible orders of addition can be employed in this process embodiment. Preferably, the formaldehyde and the cyanide source are added simultaneously to the ADA (derivative). Most preferably, the formaldehyde and the cyanide source are added in such a way that at each point in time the same molar amounts of formaldehyde and cyanide enter the reaction mixture.

In another process embodiment of the present invention, the ADA (derivative) is reacted with an acetic acid derivative which contains an activated β-C atom, such as a compound selected from the group of (salts of) $CH_2X$—COOH, $CH_2X$—CN, $CH_2X$—$CONH_2$, or mixtures thereof in the presence of a polyvalent metal ion $M^{a+}$, with X being a halogen atom.

Preferably, X is selected from the group of Cl, Br, and I, more preferably from Br and I, and most preferably X is Cl.

It is further preferred that the acetic acid derivative comprises and most preferably consists essentially of $CH_2X$—COOH. Most preferably, the acetic acid derivative is monochloroacetic acid ("MCA"). As already stated above, preferably the substituents R of the ADA (derivative) comprise and more preferably consist of —$CH_2COOH$ moieties. In this case, all reactants exclusively comprise free acid groups and it is not essential that hydrolyzing conditions are applied during the reaction. The pH in this case generally is not critical and preferably is above 6 and more preferably above 7. Further, as in this case no ammonia is generated during the reaction, the temperature is less critical than in the first described process embodiment. It generally lies between 5° C. and the boiling temperature of the reaction mixture, preferably between 10° C. and the boiling temperature of the reaction mixture, and most preferably between 25° C. and the boiling temperature of the reaction mixture.

If an ADA (derivative) or an acetic acid derivative is applied which contains nitrile and/or amide groups, the reaction must be carried out under hydrolyzing conditions for the same reasons as given above for the first process embodiment. In this case, the pH is generally chosen to be at least 9, preferably at least 10, and most preferably at least 12 during the entire reaction process. Further, if atmospheric pressure is applied, the reaction temperature preferably ranges between 25° C. and the boiling temperature of the reaction mixture, more preferably between 50° C. and the boiling temperature of the reaction mixture, still more preferably between 70° C. and the boiling temperature of the reaction mixture, and most preferably it will be in the range of 100–110° C. Lower temperatures can be applied at a lower reaction pressure.

As in the first process embodiment, the reaction proceeds directly to the complex of the polyvalent metal ion and the AD3A (derivative). Thus, also in the second process embodiment the reaction can be carried out in a single process step without making the isolation of intermediates necessary.

The second process embodiment is exemplified below for EDA, ED1A, and ED2A as starting materials.

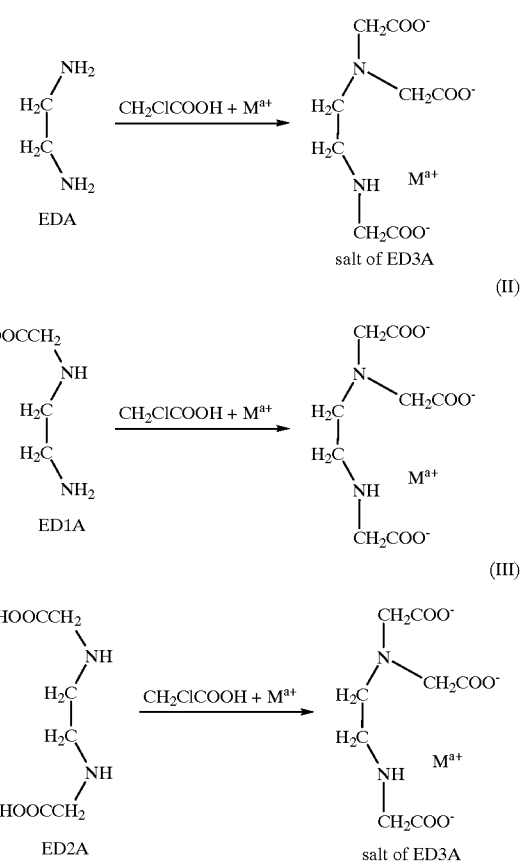

Preferably, the reactants are applied in a quantity ±10%, and more preferably ±5%, of the stoichiometric amount. Most preferably, stoichiometric amounts are applied. For the reactions illustrated above, this means that 3 moles of monochloroacetic acid are applied per mole EDA (reaction I), 2 moles of monochloroacetic acid are applied per mole ED1A (reaction II), and one mole of monochloroacetic acid is applied per mole ED2A (reaction III).

The polyvalent metal ion is added in the process of the invention in the form of a polyvalent metal source either prior to or during the addition of further reactants to the ADA (derivative).

The polyvalent metal source is preferably added in an amount of at least 60 mole %, more preferably at least 80 mole %, and most preferably at least 100 mole %, calculated as metal and based on the molar amount of ADA (derivative) present in the reaction mixture. Generally, the molar amount of the polyvalent metal will be less than 400 mole %, more preferably less than 300 mole %, and most preferably less than 200 mole %, calculated as metal and based on the molar amount of ADA (derivative) present in the reaction mixture.

Of course, also lower molar amounts of the polyvalent metal source can be applied. However, in that case only part of the resulting AD3A (derivative) will be complexed by the polyvalent metal and the uncomplexed portion will at least partially convert to AD4A (derivative). The selectivity of the process in respect of the AD3A (derivative) will then be reduced.

The polyvalent metal source preferably is a polyvalent metal salt, which preferably is at least partly water-soluble and most preferably entirely water-soluble. "At least partly water-soluble" in the sense of the present invention means that at least 0.01 g, preferably at least 0.05 g, and more preferably at least 0.1 g of the salt dissolves in 100 ml water at room temperature. An example of a partly water-soluble polyvalent metal salt is an alkaline earth metal hydroxide. This hydroxide has the advantage that it can be used at the same time as polyvalent metal source and as pH regulating agent. The polyvalent metal source can also be the salt of the polyvalent metal and the ADA (derivative), the salt of the polyvalent metal and cyanide, or the salt of the polyvalent metal and an acetic acid derivative. Preferably, the anions of the salt comprise and more preferably consist essentially of inorganic anions, such as nitrate or halide anions, with chloride being most preferred.

The polyvalent metal contained in the polyvalent metal source preferably is selected from trivalent and/or divalent metals. A suitable trivalent metal is aluminum. More preferably, the polyvalent metal consists essentially of a divalent metal, such as alkaline earth metals or transition metals such as $Mn^{2+}$, $Fe^{2+}$, $Co^{2+}$, $Ni^{2+}$, $Zn^{2+}$, or $Cu^{2+}$. Still more preferably, the polyvalent metal comprises and even more preferably consists essentially of an alkaline earth metal, such as calcium, magnesium, or barium. Most preferably, the polyvalent metal consists essentially of calcium. Suitable calcium sources are, e.g., calcium hydroxide, calcium chloride, and calcium nitrate.

Optionally, the process may comprise the further step of removing the polyvalent metal ion subsequent to the formation of the salt of the alkylene diamine triacetic acid (derivative). This can be done by any conventional means such as precipitating the polyvalent metal ion.

Precipitation can be induced, e.g., by adjusting the pH and/or by adding anions, which form a precipitate with the polyvalent metal ion. Suitable pH or temperature conditions or anions to induce precipitation will be known to the skilled person. For instance, precipitation via pH adjustment can be carried out by increasing the pH to above 8, and preferably to above 10. Precipitation via the addition of anions can be carried out, e.g., by the addition of sulfate, carbonate, phosphate or fluoride if, e.g., calcium ions are applied as polyvalent metal ions. The precipitated polyvalent metal ions can be removed by any conventional means such as filtration. After the removal of the polyvalent metal ion, the AD3A (derivative) can be isolated in its entirely protonated (three acetic acid groups), partly protonated (two acetic acid groups or one) or entirely deprotonated form. Further, if desired, the resulting AD3A may be cyclized. Suitable cyclization conditions are know to the skilled person. Typically, a temperature in the range of 5–120° C. and a pH below 13, preferably below 12, more preferably below 4, and most preferably below 2 will be applied.

The invention will be further illustrated by way of the following Examples:

EXAMPLE 1

In a 6-liter glass reactor, 567 g (6.0 moles) of monochloroacetic acid (ex Akzo Nobel) were dissolved in 1,800 g of demineralized water and 298 g (4.0 moles) of calcium hydroxide (ex Baker) were added to the solution. The pH rose from 1.0 to 11.7. Subsequently, EDA (120 g, 2.0 moles) (ex Akzo Nobel) was added within 10 minutes. The temperature was kept at about 50° C. without additional heating. After 1 h the temperature was increased to 70° C. and the resulting mixture was reacted for 5.5 h. During the entire reaction, the pH was kept constant at 7.5–8.0 by the addition of calcium hydroxide. At the end of the reaction a total of 414 g (5.6 moles) of calcium hydroxide had been added. The reaction mixture was filtered warm over a glass filter with a hyflo filter aid to remove excess of calcium hydroxide. The filtrate was allowed to cool to room temperature. After one night a precipitate had formed. Filtration yielded 447 g of the calcium salt of ED3A. This corresponds to a yield of 87%, calculated on the amount of EDA initially applied.

Removal of calcium from the ED3A:

446 g of the above product were stirred with 500 g of water. Next, 555 g of 50% sodium hydroxide (6.9 moles) were added, resulting in the precipitation of calcium hydroxide. The precipitated calcium hydroxide was filtered off on a pressure filter with the use of hyflo filter aid. The water was evaporated from the filtrate and the resulting filtrate was dried in a vacuum oven.

EXAMPLE 2

A 1-liter stainless steel reactor was charged with 60.2 g of EDA (1.0 moles) (ex Akzo Nobel), 222.4 g of calcium hydroxide (3 moles) (ex Baker), and 700 g of water. At 80° C., 81 g of hydrogen cyanide (3 moles) (ex Akzo Nobel) and 199.1 g of a 44.2% solution of formaldehyde (3.0 moles) (ex Akzo Nobel) were dosed simultaneously within 3 h. After the first hour the reaction temperature was increased to boiling. When the dosing was completed the mixture was allowed to boil for another hour and cooled to 80° C. During the dosing and reaction the pH changed from 11.0 at the beginning of the dosing to 10.0 at the end of the reaction. The resulting reaction mixture was filtrated over a hyflo filter aid to remove excess calcium hydroxide. Next, the filtrate was neutralized with sulfuric acid to pH 7.6 and seeded. Filtration and drying resulted in 78.4 g of a tan colored product containing 69.7% of ED3A, calculated on the amount of EDA initially applied. The mother liquor still contained 14.5% of ED3A, calculated on the amount of EDA initially applied.

EXAMPLE 3

In a 1 liter glass reactor, 115 g (1.21 moles) of monochloroacetic acid (ex Akzo Nobel) were dissolved in 420 g of demineralized water and 62.4 g (0.84 moles) of calcium hydroxide (ex Baker) were added to the solution. The pH rose from 1.1 to 11.2. Subsequently, PDA (propylene 1,3-diamine) (31.1 g, 0.42 moles) (ex Akzo Nobel) was added in 10 min. The temperature remained at about 50° C. without additional heating. After 1 h the temperature was increased to 70° C. and the resulting mixture was reacted for 5.5 h. During the entire reaction, the pH was kept constant at 7.5–8.0 by the addition of calcium hydroxide. At the end of the reaction a total of 25 g (0.34 moles) of calcium hydroxide had been added. The reaction mixture was filtered warm over a glass filter with a hyflo filter aid to remove the excess of calcium hydroxide. The reaction mixture contains PD3A (50.6 mole % based on PDA initially applied), PD4A (18 mole %) and PD2A (23 mole %.)

Comparative Example

A 1 liter stainless steel reactor was charged with 60.2 g of EDA (1.0 moles) (ex Akzo Nobel) and 600 g of water. At 90° C., 522.5 g of a 28.4 wt. % solution of sodium cyanide (3 moles) (ex Akzo Nobel) and 203.7 g of a 44.2 wt. % solution of formaldehyde (3.0 moles) (ex Akzo Nobel) were dosed simultaneously within 3 h. After the first hour the reaction temperature was increased to boiling. When the dosing was completed the mixture was allowed to boil for another hour and was thereafter cooled to room temperature. The 830 g of reaction mixture contained 6.0% of $Na_2ED2A$ (22 mole %, 18.9 % of Na₃ED3A (51 mole %) and 10.7% of EDTA (23 mole %). This shows that the ED2A, DE3A, and ED4A are present in a range which is in accordance with their reactivity and that the reaction does not stop in the ED3A stage.

What is claimed is:

1. A process for the preparation of alkylene diamine triacetic acid (derivatives) which comprises the conversion of an alkylene diamine (derivative) of the formula

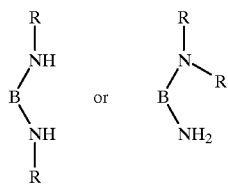

wherein B is selected from an unsubstituted or substituted alkylene bridge and R is independently selected from H or (salts of) —CH₂—COOH, —CH₂—CN, or —CH₂—CONH₂, to a salt of an alkylene diamine triacetic acid (derivative) of the formula

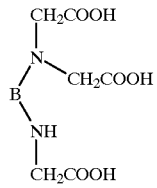

characterized in that the reaction is carried out in the presence of a polyvalent metal ion $M^{a+}$ and the entire reaction is carried out under hydrolyzing conditions if any of the reactants contain or form nitrile or amide groups, which hydrolyzing conditions are such that any nitrile and/or amide groups added to the reaction mixture or formed during the reaction is instantaneously converted to a carboxylic acid moiety or salt thereof and wherein a is the number 2 or 3.

2. The process according to claim 1, wherein B is an unsubstituted or substituted ethylene or propylene group.

3. A process for the preparation of alkylene diamine triacetic acid (derivatives) which comprises the conversion of an alkylene diamine (derivative) of the formula

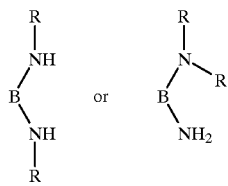

wherein B is selected from an unsubstituted or substituted alkylene bridge and R is independently selected from H or (salts of) —CH₂—COOH, —CH₂—CN, or —CH₂—CONH₂, to a salt of an alkylene diamine triacetic acid (derivative) of the formula

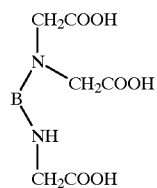

characterized in that the reaction is carried out in the presence of a polyvalent metal ion $M^{a+}$ and the entire reaction is carried out under hydrolyzing conditions if any of the reactants contain or form nitrile or amide groups, wherein the alkylene diamine (derivative) consists essentially of ethylene diamine.

4. The process according to claim 1, further comprising reacting the alkylene diamine (derivative) with formaldehyde and a cyanide source in the presence of the polyvalent metal ion under hydrolyzing conditions.

5. The process according to claim 4, wherein the reaction occurs at a pH above 10.

6. A process for the preparation of alkylene diamine triacetic acid (derivative) which comprises the conversion of an alkylene diamine (derivative) of the formula

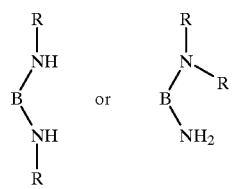

wherein B is selected from an unsubstituted or substituted alkylene bridge and R is independently selected from H or (salts of) —CH₂—COOH, —CH₂—CN, or —CH₂—CONH₂, to a salt of an alkylene diamine triacetic acid (derivative) of the formula

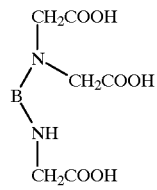

characterized in that the reaction is carried out in the presence of a polyvalent metal ion $M^{a+}$ and the entire reaction is carried out under hydrolyzing conditions if any of the reactants contain or form nitrile or amide groups, further comprising reacting the alkylene diamine (derivative) with a compound selected from the group consisting of (salts of) CH₂X—COOH, CH₂X—CN, CH₂X—CONH₂, or mixtures thereof, with X being a halogen atom.

7. The process according to claim 1, wherein the polyvalent metal ion $M^{a+}$ is a divalent metal ion.

8. The process according to claim 7, wherein the divalent metal is a Group II metal, preferably calcium.

9. The process according to claim 1, wherein the polyvalent metal ion $M^{a+}$ is added to the alkylene diamine (derivative) in the form of a metal salt which is at least partly soluble in water.

10. The process according to claim 1, wherein the polyvalent metal $M^{a+}$ is added at least in an amount equimolar to the amount of alkylene diamine (derivative) applied in the process.

11. The process according to claim 1, further comprising a step of removing the polyvalent metal ion subsequent to the formation of the salt of the alkylene diamine triacetic acid (derivative).

* * * * *

UNITED STATES PATENT AND TRADEMARK OFFICE
CERTIFICATE OF CORRECTION

PATENT NO. : 6,492,549 B2
DATED : December 10, 2002
INVENTOR(S) : Van Doorn et al.

It is certified that error appears in the above-identified patent and that said Letters Patent is hereby corrected as shown below:

<u>Title page,</u>
Item [73], Assignee, "Akzo Novel NV" should read -- Akzo Nobel NV --

Signed and Sealed this

Ninth Day of September, 2003

JAMES E. ROGAN
*Director of the United States Patent and Trademark Office*